United States Patent [19]

Lewis

[11] 4,213,457

[45] Jul. 22, 1980

[54] INTERMITTENT PATIENT SUCTION SYSTEM AND CONTROL MEANS THEREFOR

[75] Inventor: Jay L. Lewis, Knoxville, Tenn.

[73] Assignee: Robertshaw Controls Company, Richmond, Va.

[21] Appl. No.: 860,995

[22] Filed: Dec. 15, 1977

[51] Int. Cl.² .............................................. A61M 1/00
[52] U.S. Cl. ..................................... 128/276; 137/102
[58] Field of Search .................. 15/314, 315; 137/102; 128/276, 277, 278, 145.8

[56] References Cited

U.S. PATENT DOCUMENTS

| 3,653,393 | 4/1972 | Love | 137/102 |
| 3,659,605 | 5/1972 | Sielaff | 128/276 |
| 3,718,152 | 2/1973 | Kraakman | 137/102 |

FOREIGN PATENT DOCUMENTS 937068  9/1963  United Kingdom ...................... 128/278

*Primary Examiner*—Robert W. Michell
*Assistant Examiner*—J. L. Kruter
*Attorney, Agent, or Firm*—Candor, Candor & Tassone

[57] ABSTRACT

An intermittent suction system for alternately applying a vacuum and atmospheric pressure to a patient for removing fluids from the patient and comprising a vacuum source and first and second containers adapted to be interconnected to the source and to the atmospheric pressure by a control unit that is adapted to apply the vacuum to the patient in response to a vacuum condition of the first container and to apply the atmospheric pressure to the patient in response to a vacuum condition in the second container, the control unit including structure for always interconnecting the vacuum to the patient when the vacuum condition in the first container is a certain percentage of the vacuum condition of the vacuum sorce regardless of the vacuum value of the vacuum source.

10 Claims, 4 Drawing Figures

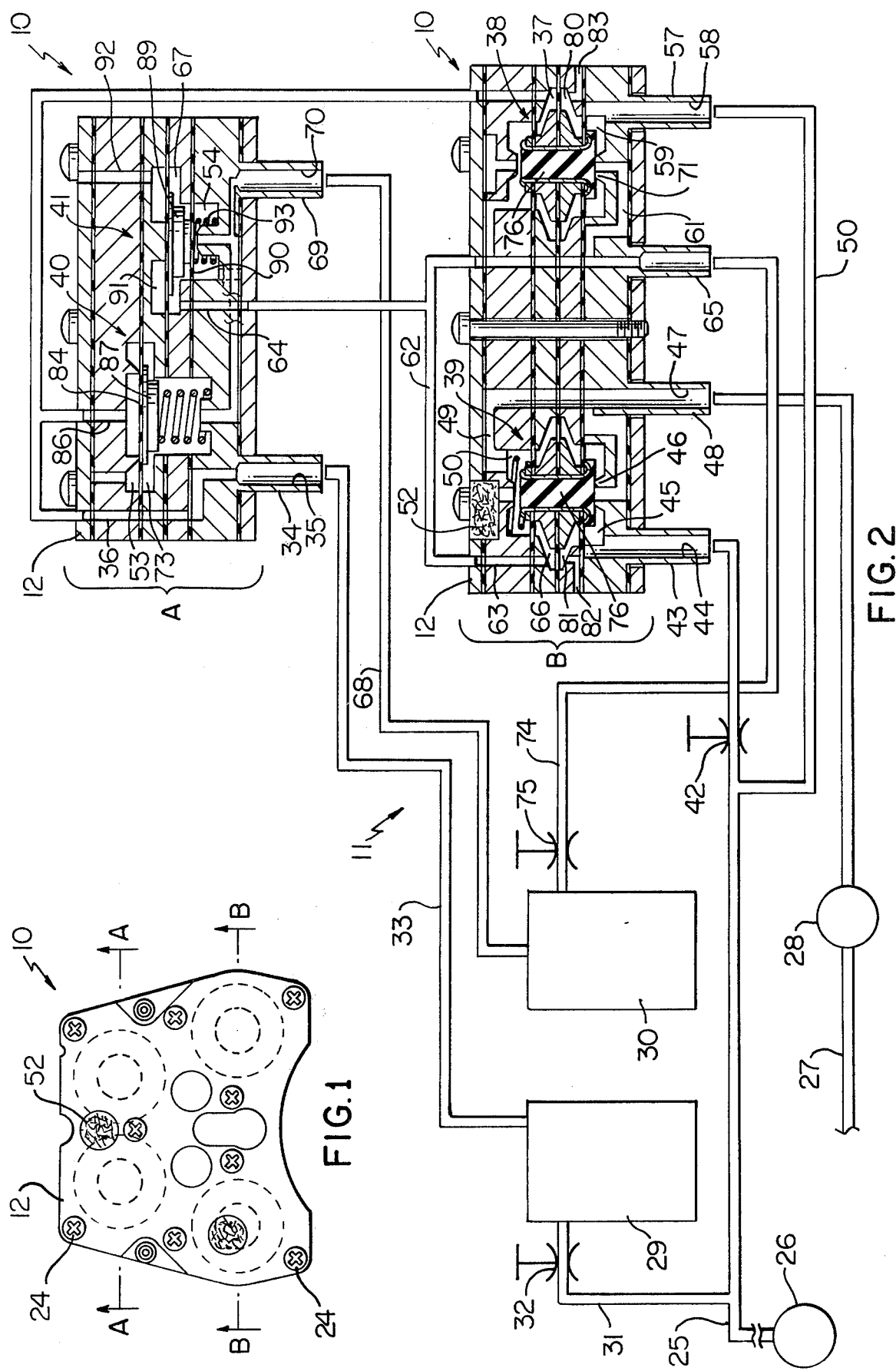

INTERMITTENT PATIENT SUCTION SYSTEM AND CONTROL MEANS THEREFOR

BACKGROUND OF THE INVENTION

1. Field of the Invention

This invention relates to an improved intermittent patient suction system and to an improved control means therefor.

2. Prior Art Statement

It is well known to provide an intermittent suction system for alternately applying a vacuum and atmospheric pressure to a patient for removing fluids from the patient and comprising a vacuum source and first and second container means adapted to be interconnected to the source and to the atmospheric pressure by control means that is adapted to apply the vacuum to the patient in response to a vacuum condition in the first container means and to apply the atmospheric pressure to the patient in response to a vacuum condition in the second container means.

For example, see the following item:

(1) U.S. Pat. No. 3,659,605—Sielaff.

It appears that the intermittent patient suction system of Item (1) above includes four like relay units in the control means thereof with each control unit including a spring means which must be overcome in order to provide the switching function for applying the vacuum to the patient as well as for applying the atmospheric pressure to the patient.

For example, see the following item:

(2) U.S. Pat. No. 3,754,572—Scott.

It appears that each of the relay logic units of Item (1) above are of the type in Item (2) above where the switching diaphragm is spring biased to one position thereof and the force of the spring must be overcome by a resulting pressure differential created by two different vacuum sources being imposed on different sized diaphragm portions thereof.

It was suggested by another that perhaps the switching relay of Item (1) could be modified so that the control means would always interconnect the vacuum to the patient when the vacuum condition of the first container means is a certain percentage of the vacuum condition of the sorce regardless of the vacuum value of the source.

However, such suggestion did not provide any information as to how the physical structure of such relay of Item (1) above and as of the construction of Item (2) above could be modified to produce such desired results.

SUMMARY OF THE INVENTION

It is a feature of this invention to provide an intermittent patient suction system wherein suction will be applied to the patient when a vacuum condition in the system reaches a certain percentage of the vacuum condition of the main vacuum source regardless of the vacuum value of the main vacuum source.

In particular, most hospitals each provide a main vacuum source that is directed to various treating rooms whereby an individual control system being utilized in a particular room must include a vacuum regulator therein so as to regulate the vacuum from the main vacuum source to the desired level for the particular control system because the vacuum value of the main vacuum source for the hospital can vary over a large range thereof depending upon the amount of use being made thereon by the various vacuum systems in the hospital at any one time.

However, it was found that even when such a regulator is being utilized, the vacuum value of the main vacuum source of the hospital may fall to a value which will not permit the regulator to supply any control vacuum to the control system and therefore will cause an adverse interruption in the use of that particular control system.

Thus, the above feature of this invention readily permits a particular intermittent patient suction system to operate regardless of the vacuum value of the main vacuum source of the hospital since such system merely operates on a percentage basis of vacuum values and not on any particular vacuum value as in the system of the aforementioned U.S. patent to Sielaff, U.S. Pat. No. 3,659,605.

Accordingly, one embodiment of this invention provides an intermittent suction system for alternately applying a vacuum and atmospheric pressure to a patient for removing fluids from a patient and comprising a vacuum source and first and second container means adapted to be interconnected to the source and atmospheric pressure by a control means that is adapted to apply the vacuum to the patient in response to a vacuum condition of the first container means and to apply the atmospheric pressure to the patient in response to a vacuum condition in the second container means, the control means having means for always interconnecting the vacuum to the patient when the vacuum condition in the first container means is a certain percentage of the vacuum condition of the source regardless of the vacuum value of the source.

Such system of this invention can also include means of the control means for always interconnecting the atmospheric pressure to the patient when the vacuum value in the second container means is a certain percentage of the vacuum value in the first container means.

Accordingly, it is an object of this invention to provide an improved intermittent patient suction system having one or more of the novel features of this invention as set forth above or hereinafter shown or described.

Another object of this invention is to provide an improved control means for such an intermittent patient suction system or the like, the control means of this invention having one or more of the novel features of this invention as set forth above or hereinafter shown or described.

Other objects, uses and advantages of this invention are apparent from a reading of this description which proceeds with reference to the accompanying drawings forming a part thereof and wherein:

BRIEF DESCRIPTION OF THE DRAWING

FIG. 1 is a top view of the improved control means of this invention.

FIG. 2 is an enlarged schematic view illustrating the control means of FIG. 1 utilized in the intermittent patient suction system of this invention, the control means of FIG. 2 comprising sections taken on lines A—A and B—B of FIG. 1 and with such sections being respectively labeled A and B in FIG. 2.

DESCRIPTION OF THE PREFERRED EMBODIMENT

Figure 3:
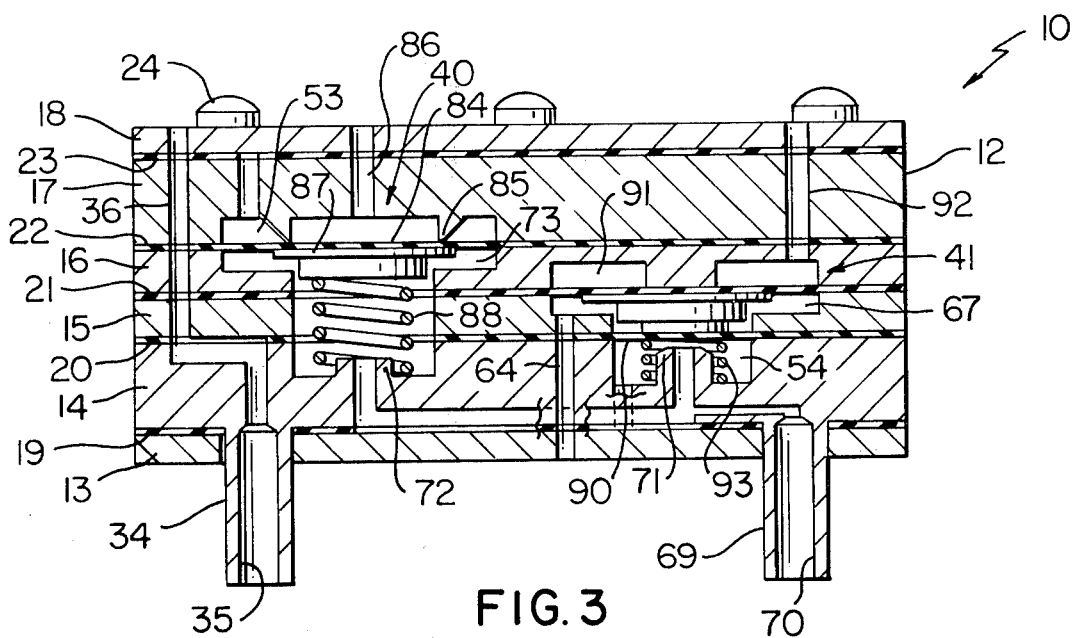
FIG. 3 is an enlarged view of the section A of the control unit of FIG. 1.
Figure 4:
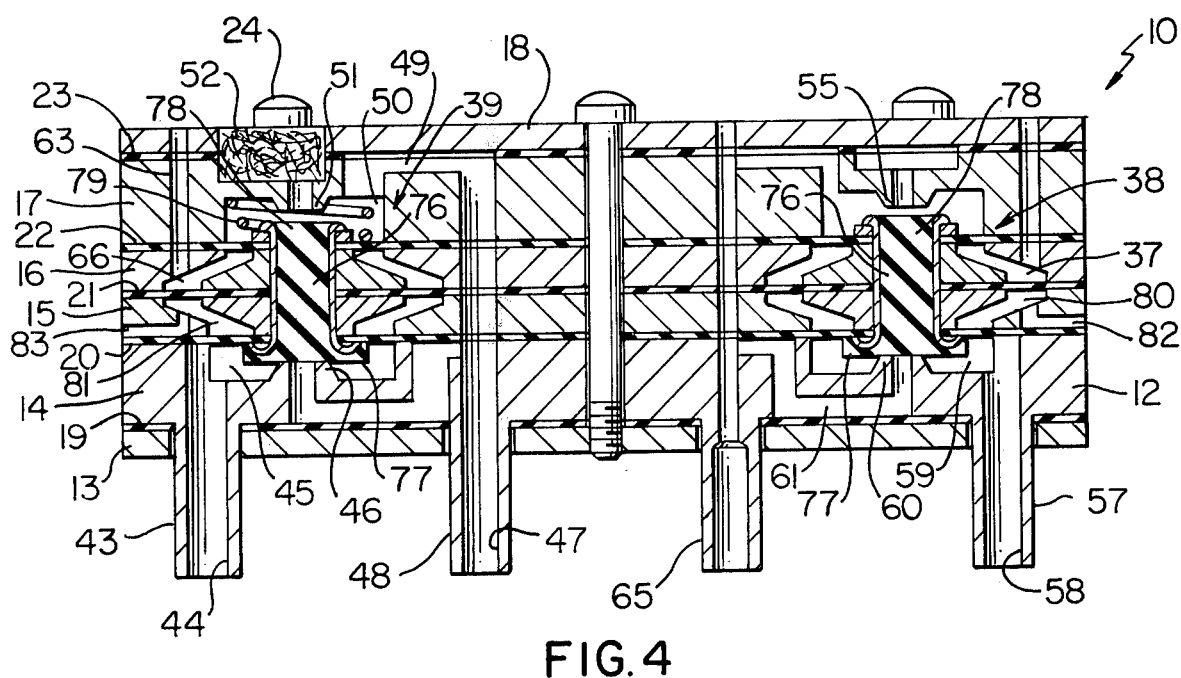
FIG. 4 is an enlarged view of the section B of the control unit of FIG. 2.

While the various features of this invention are hereinafter described and illustrated as being particularly adapted to provide a control means for an intermittent patient suction system, it is to be understood that the various features of this invention can be utilized singly or in any combination thereof to provide control means for other systems as desired.

Therefore, this invention is not to be limited to only the embodiment illustrated in the drawings because the drawings are merely utilized to illustrate one of the wide variety of uses of this invention.

Referring now to FIGS. 1 and 2, the improved control means of this invention is generally indicated by the reference numeral 10 and is utilized for providing the control means for an intermittent patient suction system of this invention that is generally indicated by the reference numeral 11 in FIG. 2.

While the control means 10 of this invention is illustrated as being a self-contained unit formed by a housing means 12 having a plurality of plates 13, 14, 15, 16, 17 and 18 suitably stacked together with a plurality of flexible diaphragms 19, 20, 21, 22 and 23 disposed therebetween and all held together by a plurality of fastening means 23, it is to be understood that the control means 10 of this invention can comprise a plurality of separate relay units suitably interconnected together by conduit means or the like whereby this invention is not to be limited to the control means being a self-contained unit.

However, the self-contained unit 10 of this invention readily permits the same to be utilized in already existing control systems for replacing the individual relay units thereof, such as the individual relay units of the aforementioned U.S. patent to Sielaff, U.S. Pat. No. 3,659,605, to cause such system to function in the improved manner as provided by the system 11 of this invention and hereinafter described.

The improved intermittent patient suction system 11 of this invention includes a vacuum source conduit 25 for interconnecting to a main vacuum source 26, such as the main vacuum source for a hospital, and a conduit means 27 for interconnecting to a hospital patient for withdrawing fluids therefrom in a manner well known in the art, such as is described in the aforementioned U.S. patent to Sielaff, U.S. Pat. No. 3,659,605, the conduit means 27 having a vacuum regulator 28 therein so that the value of its vacuum being applied to a patient through the conduit means 27 will not exceed a safe value.

The system 11 includes a first container means 29 and a second container means 30, the vacuum source conduit means 25 being interconnected to the interior of the first container means 29 by a branch conduit means 31 that has an adjustable restrictor means 32 therein.

The first container means 29 also has its interior interconnected by a conduit means 33 to a nipple 34 of the control unit 10, the nipple 34 having a passage means 35 that interconnects with an internal passage means 36 in the housing means 12 and leads to a control chamber 37 of a relay unit of the control means 12 that is generally indicated by the reference numeral 38 in FIG. 2.

The control unit 10 also includes three other relay units which are respectively and generally indicated by the reference numerals 39, 40 and 41 with each including one or more internal valve seat adapted to be opened and closed by a movable valve member that is carried by or controlled by a portion of one or more of flexible diaphragms 20, 21 and 22 as fully illustrated in the drawing, whereby only the details of the relay means 38–41 necessary to fully understand the features of this invention will be described.

The vacuum source conduit means 25 of the system 11 has an adjustable restrictor means 42 therein and is interconnected to another nipple 43 of the control unit 10 that has a passage 44 therein that leads to a chamber 45 of the relay unit 38, the chamber 45 being adapted to be interconnected to a valve seat 46 of the relay unit 39 that leads to a passage means 47 of another nipple 48 of the control unit 10.

The nipple 48 is interconnected to the patient conduit means 27 as illustrated and is also fluidly interconnected to an internal passage means 49 of the control unit 10 that leads to another chamber 50 of the relay unit 39, the chamber 50 being adapted to be interconnected to a valve seat 51 of the relay unit 39 that is fluidly interconnected to a vent or an atmospheric pressure chamber 52 that supplies atmospheric pressure through a suitable filter not only to the valve seat 51, but also to a chamber 53 of the relay unit 49, to a chamber 54 of the relay unit 41 and to a valve seat 55 of the relay unit 38 for a purpose hereinafter described.

A branch conduit means 56 interconnects to the vacuum source conduit means 25 intermediate the variable restrictor means 42 thereof and the source 26 to interconnect the vacuum source conduit means 25 to a nipple 57 of the control unit 10 that has a passage 58 therein leading to a chamber 59 of the relay unit 38, the chamber 59 being adapted to be interconnected to a valve seat 60 which, through internal passage means 61, 62, 63 and 64, is adapted to be fluidly interconnected to a nipple 65 of the control unit 10, to a control chamber 66 of the relay unit 39 and to a control chamber 67 of the relay unit 41 for a purpose hereinafter described.

The interior of the second container means 30 is interconnected by the conduit means 68 to a nipple 69 of the control unit 10 that has a passage 70 therein leading to not only a valve seat 71 of the relay unit 41, but also to a valve seat 72 of the relay unit 40, the valve seat 72 of the relay unit 40 always being open and thereby being continuously interconnected to a control chamber 73 of the relay unit 40 for a purpose hereinafter described.

The interior of the second container means 30 is also interconnected by a conduit means 74, which has an adjustable restriction means 75 therein, to the nipple 65 of the control unit 10 that is in fluid communication with the internal passage means 62 previously described.

The relay units 38 and 39 of the control unit 10 of this invention each includes a like resilient valve member 76 being carried by portions of the three flexible diaphragms 20, 21 and 22 whereby the ends 77 of the resilient valve members 76 are adapted to respectively open and close the valve seats 60 and 46 while the other ends 78 thereof are adapted to respectively open and close the valve seats 55 and 51 for a purpose hereinafter described.

While no auxiliary spring means operates on the valve member 76 of the relay unit 38 for a reason hereinafter described, a small compression spring 79 can be disposed in the control chamber 50 of the relay unit 39 to operate on the valve member 78 to tend to urge the same in a direction to close the valve seat 46 for a purpose hereinafter described.

The valve members 76 of the relay units 38 and 39 cooperate with the diaphragms 20 and 21 to respectively define chambers 80 and 81 opposite to the control chambers 37 and 66 thereof with the chambers 80 and 81 respectively being interconnected to the atmosphere by passage means 82 and 83.

A portion of the diaphragm 22 for the relay unit 40 acts as a valve member 84 for opening and closing a valve seat 85 of the relay unit 40 which projects into the chamber 53 thereof and is interconnected by a passage means 86 to the internal passage means 36 of the control unit 10. A rigid backup member 87 is provided for the valve member 84 of the relay unit 40 with the valve member 84 normally being urged to the closed position thereof by a compression spring 88 disposed in the chamber 73 thereof and bearing against the backup member 87.

A spacing member 89 is disposed between portions of the diaphragms 20 and 21 of the relay unit 41 as illustrated whereby a portion of the diaphragm 20 forms a valve member 90 for opening and closing the valve seat 71, the spacer 89 being disposed in the chamber 87 of the relay unit 41.

A portion of the diaphragm 21 forms a chamber 91 of the relay unit 41 opposite from the chamber 67 thereof, the chamber 91 being interconnected to the atmosphere by a passage 92 as illustrated.

A small compression spring 93 is disposed in the chamber 54 of the relay unit 41 to tend to move the valve member 90 away from the valve seat 41 as illustrated.

From the above, it can be seen that the self-contained control unit 10 of this invention can be formed in a relatively simple manner to provide a single package containing the relay units 38, 39, 41 and 41 to operate in the improved system 11 of this invention in a manner now to be described.

When the system 11 is initially interconnected to the vacuum source 26 by the conduit means 25 and the conduit means 27 is interconnected to the patient, the vacuum now being created in the chamber 59 of the relay unit 39, in effect, pulls downwardly on the effective portion of the diaphragm 20 to hold the valve member 76 in a closed condition against the valve seat 60 while the spring 79 of the relay means 39 maintains the valve member 76 against the valve seat 46 to thereby prevent the vacuum source conduit 25 that is interconnected to the chamber 45 of the relay unit 39 through the adjustable restrictor 42 from being interconnected to the patient conduit 27 through the valve seat 46 of the relay unit 39. At this time, the patient conduit 27 is interconnected to atmospheric pressure because the passage means 49 receives atmospheric pressure from the chamber 51 of the relay unit 39 as the valve seat 51 is in an open condition as illustrated in FIG. 2.

Also, at this time, the control chamber 66 of the relay unit 39 is at atmospheric pressure because the passages 62 and 74 interconnect to the open vent valve seat 55 of the relay unit 38. Also, the second container means 30 is at atmospheric pressure because the valve seat 71 of the relay unit 41 is open as illustrated in FIG. 2 and then the passage 68 is interconnected to the vent chamber 54 of the relay unit 41.

Nevertheless, the vacuum source 26 is continuously evacuating the first container means 29 through the branch conduit means 31 and its adjustable restrictor means 32 whereby this reduction of the pressure in the first container means 29 also causes, by means of the conduit means 33 and internal passage means 36 of the control unit 10, an evacuation of the control chamber 37 of the relay unit 38.

The size of the effective portion of the intermediate diaphragm 21 of the relay unit 38 and the effective portion of the diaphragm 20 of the relay unit 30 have been so selected that the valve member 76 will remain closed against the valve seat 60 until the vacuum value in the chamber 37 reaches a certain percentage of the vacuum value in the chamber 59 regardless of the vacuum value in the chamber 59 and, thus, regardless of the vacuum value of the main vacuum source 26.

In the embodiment of the control system 11 illustrated in the drawings, the relay unit 38 has been so constructed and arranged that when the vacuum value being created in the first container means 29 and, thus, in the control chamber 37 of the relay unit 38 reaches approximately 50% of the vacuum value of the vacuum source 26 and, thus, the vacuum value in the chamber 59 of the relay unit 38, the valve member 76 is switched from the condition illustrated in FIG. 2 to move upwardly and open the valve seat 60 while closing the valve seat 55, such switching of the valve member 76 taking place solely on the pressure differential across the relay unit 38 as no auxiliary springs are utilized in the relay unit 38 that would have to have the force thereof overcome before switching.

The closing of the valve seat 55 of the relay unit 38 disconnects the atmosphere from the control chamber 66 of the relay unit 39 while, in effect, interconnecting the vacuum source 26 to the control chamber 66 of the relay unit 39 by means of the now opened valve seat 60 and interconnecting passage means 62 and 63 whereby the valve member 76 of the relay unit 39 is moved upwardly by the vacuum now being created in the control chamber 66 that overcomes the force of the compression spring 79 as well as the vacuum in the chamber 45 acting on the effective portion of the lower diaphragm 20 of the relay unit 39.

The upward movement of the valve member 76 of the relay unit 39 cause the valve member 76 to open the valve seat 46 and close the valve seat 51 whereby the chamber 50 is now evacuated to hold the valve member 76 in an upward position thereof because the vacuum source conduit 25, through the restrictor means 42, is now interconnected through the opened valve seat 46 to the chamber 50 of the relay unit 38.

The vacuum source conduit 25 is also interconnected through the now opened valve seat 46 of relay unit 39 to the patient conduit means 27 through the regulator 28 to begin a suction operation on the patient and thereby withdraw fluid therefrom for a certain increment of time that is based on the amount of time it takes for the second container means 30 to be evacuated to reach a certain vacuum value that is a certain percentage of the vacuum value in the first container means 29 as will be apparent hereinafter.

In particular, the opening of the valve seat 60 of the relay unit 38 to interconnect the vacuum source conduit means 25 to the internal passage means 61 also interconnects the vacuum source conduit means 25 to the nipple 65 and through conduit means 74 to the interior of the second container means 30 to begin to evacuate the same through the adjustable restrictor means 75 of the conduit means 74 because the valve seat 71 of the relay unit 41 is now closed by its valve member 90 to disconnect the vent chamber 54 from the interior of the second container means 30.

In particular, when the control chamber 66 of the relay unit 39 is evacuated in the above manner, an evacuation of the control chamber 67 of the relay unit 41 also takes place by means of the interconnecting passage means 63 whereby the resulting pressure differential across the larger effective portion of the diaphragm 22 of the relay unit 41 causes the valve member 90 to move downwardly in FIG. 2 and close the valve seat 71 in opposition to the force of the spring 93.

As the second container means 30 is being evacuated in the above manner, such evacuation of the interior of the second container means 30 is also being sensed in the chamber 73 of the relay unit 40 by means of the conduit means 68, nipple 69, passage 70 and open valve seat 72 of the relay unit 40 whereby the evacuation of the chamber 73, in effect, tends to act on the effective portion of the diaphragm 22 of the relay unit 40 to pull the valve member 84 downwardly not only in opposition to the force of the compression spring 88, but also in opposition to the force of the vacuum in the valve seat 85 which is the same vacuum value of the vacuum being created in the first container means 29 because the interior of the first container means 29 is interconnected to the valve seat 85 by means of the conduit 33, nipple 34, passage 35 and passage 36.

Accordingly, when the vacuum value in the second container means 30 reaches a certain percentage of the vacuum value in the first container means 29, which in the embodiment of the control system 11 illustrated in FIG. 2, is approximately 50%, the valve member 84 of the relay unit 40 is moved downwardly to open the valve seat 85 and thereby interconnect not only the interior of the first container means 29 to atmospheric pressure by means of the passage 53, but also to interconnect the control chamber 37 of the relay unit 37 to atmospheric pressure by the passage 53 through the passage means 36.

Thus, the dumping of the vacuum in the control chamber 37 of the relay unit 38 causes the valve member 76 thereof to be drawn downwardly by the vacuum in the chamber 59 thereof and thereby close the valve seat 60 and to not only disconnect the vacuum source conduit 25 from the valve seat 60 and, thus, from the control chamber 66 of the relay unit 39, but also, through the opening of the valve seat 55, to dump the vacuum in the control chamber 66 of the relay unit 39 to atmosphere through the now opened valve seat 55 whereby the valve member 76 of the relay unit 39 moves downwardly to close the valve seat 45 and open the valve seat 51 and thereby terminate the interconnection of the vacuum source conduit 25 through the valve seat 46 to the patient conduit 27. The dumping of the vacuum in the control chamber 65 of the relay unit 39 also dumps the vacuum in the control chamber 67 of the relay unit 41 whereby the valve member 90 of the relay unit 41 moves upwardly in FIG. 2 to open the valve seat 71 and thereby again interconnect the vent chamber 54 of the relay unit to the interior of the second container means 30 to dump the vacuum therein. The opening of the valve seat 71 of the relay unit 41 also now dumps the vacuum in the chamber 73 of the relay unit 40 to thereby cause the valve means 84 to move against the valve seat 85 to disconnect the interior of the first container means 29 from the vent chamber 52 of the relay unit 40.

At this time, the patient conduit 27 is now interconnected to atmospheric pressure by the opened valve seat 51 of the relay unit 39 so that withdrawn patient fluid in the patient conduit 27 now can partially flow backwardly to the patient for the reasons fully set forth in the aforementioned U.S. patent to Sielaff, U.S. Pat. No. 3,659,605, until the vacuum value in the first container means 29 again reaches the previously described certain percentage of the vacuum value of the vacuum source 26 to again cause the relay unit 38 to move the valve member 76 thereof upwardly and thereby again interconnect the vacuum source 26 to the patient conduit means 27 through the relay unit 39 in the manner previously described.

From the above, it can be seen that the system 11 and the control unit 10 of this invention will intermittently interconnect the vacuum source 26 to the patient conduit 27 for a certain time period and then interconnect the atmospheric pressure to the patient conduit means 27 for a certain time period in a continuous cycling manner as long as the control system 11 is interconnected to the vacuum source 26 through the conduit means 25, the volume size of the container means 29 and 30 and the adjustment of the restrictor means 82 and 75 being such that the vacuum source 26 is interconnected to the patient conduit means 27 for approximately fifteen seconds while the atmospheric pressure is interconnected to the patient conduit means 27 for approximately seven and one half seconds.

From the above, it can be seen that the control system 11 and control means 10 of this invention therefor will provide the aforementioned cycling operation of interconnecting the vacuum source 26 to the patient conduit 27 for a certain time period and the atmospheric pressure to the patient conduit 27 for a certain time period regardless of the vacuum value of the vacuum source 26 because such switching operation is merely based on the vacuum value in the first container means 29 being a certain percentage of the vacuum value of the main vacuum source 26 and not on a specific value thereof as is required by the spring switching means of the relays of the aforementioned U.S. patent to Sielaff, U.S. Pat. No. 3,659,605.

In addition, the changing from the interconnection of the vacuum source 26 to the patient conduit 27 to the interconnection of the atmospheric pressure to the patient conduit 27 is also merely dependent upon the vacuum value of the second container means 30 becoming a certain percentage of the vacuum value in the first container means 29 whereby the control system 11 of this invention will operate with any vacuum value of the main vacuum source 26 so that the system 11 will function whether the vacuum value of the main source 26 of the hospital is high or low or continuously varying.

Therefore, this invention not only provides an improved intermittent patient suction system, but also this invention provides an improved control means for such a system or the like.

While the forms of the invention now preferred have been illustrated and described as required by the Patent Statute, it is to be understood that other forms can be utilized and still fall within the scope of the appended claims.

What is claimed is:

1. In a control means for an intermittent suction system and having output means for alternately applying a vacuum and atmospheric pressure to a patient for removing fluids from said patient and wherein said system includes a vacuum source and first and second container means adapted to be interconnected to operating means of said control means and to said source and said atmospheric pressure by said operating means of said control means that is adapted to apply said vacuum through said output means to said patient in response to a vacuum condition of said first container means and to apply said atmospheric pressure through said output means to said patient in response to a vacuum condition in said second container means, the improvement comprising means in said operating means of said control means for always being adapted to interconnect said vacuum through said output means to said patient when said vacuum condition in said first container means is a certain percentage of the vacuum condition of said source regardless of the vacuum value of said source, so as to prevent any adverse interruption in said system during the use thereof for said patient should the vacuum level of said source fall to an undesirable level.

2. A control means as set forth in claim 1 wherein said certain percentage is approximately 50 percent.

3. A control means as set forth in claim 1 wherein said operating means of said control means includes means for always being adapted to interconnect said atmospheric pressure to said patient when said vacuum condition in said second container means is a certain percentage of the vacuum condition in said first container means.

4. A control means as set forth in claim 3 wherein said certain percentage of said vacuum condition in said first container means is approximately 50% percent.

5. A control means as set forth in innclaim 1 wherein said control means comprises a self-contained unit.

6. In a control means for an intermittent suction system and having output means for alternately applying a vacuum and atmospheric pressure to a patient for removing fluids from said patient and wherein said system includes a vacuum source and first and second container means adapted to be interconnected to operating means of said control means and to said source and said atmospheric pressure by said operating means of said control means that is adapted to apply said vacuum through said output means to said patient in response to a vacuum condition of said first container means and to apply said atmospheric pressure through said output means to said patient in response to a vacuum condition in said second container means, the improvement comprising means in said operating means of said control means for always being adapted to interconnect said vacuum through said output means to said patient when said vacuum condition in said first container means is a certain percentage of the vacuum condition of said source regardless of the vacuum value of said source, said operating means of said control means including means for always being adapted to interconnect said atmospheric pressure to said patient when said vacuum condition in said second container means is a certain percentage of the vacuum condition in said first container means, said certain percentage of said vacuum condition in said first container means being approximately 50 percent, said certain percentage of said vacuum condition of said source being approximately 50 percent.

7. In a control means for an intermittent suction system and having output means for alternately applying a vacuum and atmospheric pressure to a patient for removing fluids from said patient and wherein said system includes a vacuum source and first and second container means adapted to be interconnected to operating means of said control means and to said source and said atmospheric pressure by said operating means of said control means that is adapted to apply said vacuum through said output means to said patient in response to a vacuum condition of said first container means and to apply said atmospheric pressure through said output means to said patient in response to a vacuum condition in said second container means, the improvement comprising means in said operating means of said control means for always being adapted to interconnect said vacuum through said output means to said patient when said vacuum condition in said first container means is a certain percentage of the vacuum condition of said source regardless of the vacuum value of said source, said means of said operating means of said control means for always being adapted to interconnect comprising a relay valve means having a valve seat and a movable valve member for opening and closing said valve seat and being adapted to be responsive to said vacuum source and to said vacuum condition of said first container means.

8. A control means as set forth in claim 7 wherein said relay valve means has flexible diaphragm means carrying said valve member, said relay valve means having means adapted for imposing said vacuum source against one side of said diaphragm means and said vacuum condition of said first container means against the other side of said diaphragm means.

9. A control system as set forth in claim 8 wherein said diaphragm means of said relay valve means comprises a plurality of flexible diaphragms.

10. A control system as set forth in claim 9 wherein said control means includes other relay valve means and a single housing means containing all of said relay valve means therein to define a self-contained unit.

* * * * *